United States Patent [19]

Fischer et al.

[11] Patent Number: 5,169,758
[45] Date of Patent: Dec. 8, 1992

[54] STABILIZED, NAD(P)H-DEPENDENT, SOLUBLE NITRATE REDUCTASE, A PROCESS FOR THE PREPARATION THEREOF AND A REAGENT CONTAINING IT

[75] Inventors: Stephan Fischer, Weilheim; Bärbel Wurst, Pöcking; Hans-Otto Beutler, Tutzing; Georg-Burkhard Kresse, Penzberg; Herwig Brunner, Weilheim, all of Fed. Rep. of Germany

[73] Assignee: Boehringer Mannheim GmbH, Mannheim-Waldhof, Fed. Rep. of Germany

[21] Appl. No.: 561,358

[22] Filed: Aug. 1, 1990

Related U.S. Application Data

[63] Continuation of Ser. No. 45,830, May 1, 1987, abandoned.

[30] Foreign Application Priority Data

May 2, 1986 [DE] Fed. Rep. of Germany ....... 3614838

[51] Int. Cl.$^5$ .............. C12Q 1/26; C12N 9/06
[52] U.S. Cl. ...................... 435/25; 435/37; 435/188; 435/189; 435/184; 435/191
[58] Field of Search ............ 435/25, 37, 188, 189, 435/184, 191, 803, 810, 814, 815, 816

[56] References Cited

U.S. PATENT DOCUMENTS 3,764,478 10/1973 Bergmeyer ................... 195/99
4,587,220 5/1986 Mayambala-Mwanika et al. ........................ 435/175
4,663,288 5/1987 Lloyd et al. ................. 435/814

OTHER PUBLICATIONS

Minagawa et al. *J. Biochem.*, vol. 91, 761–774 (1982).
Sigma Catalog, 1987, pp. 306 and 703.
Enzyme Nomenclature, 1979, Academic Press.
Downey et al, J. Bacteriology, vol. 137, pp. 105–114 (1979).
The Proceedings of Biotechnology, Band 1, 1984, Seiten 379–390; P. Monsan et al.: "Stabilization of enzyme activity".
Methods of Enzymatic Analysis, Band VII, Edition 3, 1985, Seiten 578–585: S. Taniguchi et al.: "Nitrate".

*Primary Examiner*—David L. Lacey
*Assistant Examiner*—Laurie Scheiner
*Attorney, Agent, or Firm*—Felfe & Lynch

[57] ABSTRACT

The present invention provides a stabilized, NAD(P)H-dependent, soluble nitrate reductase of the assimilatory type, characterized by a molecular weight of about 90,000 D in the case of electrophoresis in the presence of sodium dodecyl sulphate and a residual activity after 3 weeks at 35° C. of more than 60%, obtainable by preparing a suspension of the comminuted starting material in tris/tartaric acid buffer (pH 7–8.5), adding soluble polyethyleneimine thereto in such an amount that 10 to 20% of the nitrate reductase activity passes into the precipitation obtained, separating off the precipitate and working up the supernatant according to conventional biochemical methods of fractionation in the above-mentioned digestion buffer, dialyzing the enzyme solution obtained and lyophilizing in a zwitterionic buffer.

13 Claims, No Drawings

STABILIZED, NAD(P)H-DEPENDENT, SOLUBLE NITRATE REDUCTASE, A PROCESS FOR THE PREPARATION THEREOF AND A REAGENT CONTAINING IT

This application is a continuation of application Ser. No. 045,830, filed May 1, 1987, now abandoned.

The present invention is concerned with a stabilised, NAD(P)H-dependent soluble nitrate reductase, with a process for the preparation thereof and with the use thereof.

The determination of nitrate is one of the elementary analytic tasks in foodstuff chemistry. A large number of analytic methods is known which are used for the determination of the nitrate content in foodstuff chemistry (see, for example, "Handbuch der Lebensmittelchemie", II/2, pub. Springer Verlag, 1967). However, all known methods of analysis suffer from the disadvantage of being very laborious and time-consuming. The direct methods of determination are frequently insensitive and not very specific. Therefore, in practice, nitrate determinations are carried out by first reducing the nitrate ion and subsequently determining the reduction product according to a method of high specificity. It is necessary for the chemical determination of nitrate that it must first be reduced with a reducing agent to nitrite. Of the large number of conventional reducing agents, only the use of a cadmium reducing agent has proved to be useful. However, the use of cadmium is regarded as being extremely problematic since even small amounts of cadmium are toxic and cancerogenic.

Many attempts have already been made to replace cadmium by some other reducing agent. However, hitherto no other suitable reducing agent has been found. There is, therefore, a great interest in finding a specific enzymatic method.

Five enzymes are known which react with nitrate in a photometrically measurable reaction.

Nitrate reductase (E.C. 1.9.6.1) reduces nitrate in the presence of ferrocytochrome; nitrate reductase (E.C. 1.7.99.4) requires for the nitrate reaction a reduced acceptor, for example methyl viologen and three further enzymes are known which reduce nitrate in the presence of NADH, NADPH and NAD(P)H.

All these enzymes are described in detail in the literature. In about 200 literature references, there are described preparations from various animal, vegetable and microbial sources, possibilities of purification, kinetic properties and the physiological importance in the living cell. Of these, there are two publications in which there is also suggested a nitrate determination with nitrate-reacting enzymes:

In Anal. Chem., 50, 1319/1978, there is mentioned the reduction of nitrate with a nitrate reductase; however, the nitrite formed is determined electrochemically after the use of the nitrate reductase.

For the determination of nitrate in meat and fish products, Hamano et al., in Agr. Biol. Chem., 47, 2427/1983, used a nitrate reductase (E.C. 1.7.99.4), the nitrite formed being measured in a substantially specific diazotisation reaction.

The use of an enzyme which is able to reduce nitrate in the presence of NADH, NADPH or NAD(P)H has hitherto not been successful for the determination of nitrate. The reasons for this may well be the great instability of the enzyme, whereby, in particular, the property of the enzyme to reduce nitrate by means of the mentioned co-enzymes is very unstable and, as a rule, is already lost within the space of a few hours although the enzyme can still utilise other reducing agents which cannot be determined directly. However, a particular difficulty also lies in the fact that this enzyme also displays a nitrite reductase activity which leads to a further reduction of the nitrite formed and, therefore, does not permit an end point determination by measurement of the nitrite formed. In Z. Pflanzenphysiol., 66, 290-293/1972 there is admittedly already described a nitrate determination with nitrate reductase from spinach leaves, whereby either oxidised NADH or nitrite formed is said to be measurable but the measurement of the nitrite is recommended and not that of NAD. However, a repetition of this process did not give any useful results.

Therefore, it is an object of the present invention to provide a process for the determination of nitrate in which the disadvantages and difficulties of the previously described processes are avoided and a direct determination of the conversion of NAD(P)H into NAD(P) can take place within a short period of time as a measure of the nitrate reduced by the nitrate reductase. It is also an object of the present invention to provide an appropriate enzyme and reagent for this process.

Thus, according to the present invention, there is provided a stabilised, NAD(P)H-dependent, soluble nitrate reductase of the assimilatory type, characterised by a molecular weight of about 90,000 D in the case of electrophoresis in the presence of sodium dodecyl sulphate and a residual activity after 3 weeks at 35° C. of more than 60%, obtainable by preparing a suspension of the comminuted starting material in tris/tartaric acid buffer (pH 7-8.5), adding soluble polyethyleneimine thereto in such an amount that 10 to 20% of the nitrate reductase activity passes into the precipitate obtained, separating off the precipitate and working up the supernatant according to conventional biochemical methods of fractionation in the above-mentioned digestion buffer, dialysing the enzyme solution and lyophilising in a zwitterionic buffer.

The enzyme used according to the present invention (E.C. 1.6.6.2) displays a substantially improved stability of its reductase activity with NAD(P)H as co-enzyme and can be used not only in a lyophilised state but also in a reconstituted state in aqueous solution for nitrate determination without a disturbing nitrite reductase effectiveness occurring.

The preparation of the stabilised, NAD(P)H-dependent, soluble nitrate reductase preparation of the assimilatory type according to the present invention from biological material takes place by comminution, digestion in a neutral to weakly alkaline medium and fractionation in the presence of a complex former and of a mercaptan, wherein a suspension of the comminuted starting material is prepared in tris/tartaric acid buffer (pH 7-8.5), soluble polyethyleneimine is added thereto in such an amount that 10 to 20% of the nitrate reductase activity passes over into the precipitate obtained, the precipitate is separated off and the supernatant is worked up according to conventional biochemical fractionation methods in the above-mentioned digestion buffer and the enzyme solution obtained is dialysed and lyophilised in a zwitterionic buffer.

Important for the achievement of the desired properties is the use of the special buffer, the polyethyleneimine fractionation under conditions which do not give a quantitative retention of the enzyme in the dissolved phase, as well as the lyophilisation of the enriched, stabilised enzyme obtained in a zwitterionic buffer.

The digestion buffer based on tris/tartaric acid has a pH value of from 7 to 8.5 and preferably a concentration of from 10 to 100 mmole/liter. More preferably, there is used a 30 to 70 mmolar tris/tartaric acid buffer solution with a pH value of from 7.2 to 8.0.

As starting material, there can be used the known biological materials which contain the NAD(P)H-dependent nitrate reductase of the assimilatory type. It is preferred to start from a mould fungus, especially *Asperqillus niger*. As starting material, it is especially preferred to use Ascerqillus sp. DSM 1729 or *Aspercillus nidulans* DSM 63358.

A protease inhibitor is preferably added to the buffer used, in which case there can be used a known protease inhibitor, preferably benzamidine and/or PMSF. Furthermore, a sugar or sugar alcohol is preferably added to the buffer, the concentration thereby preferably being up to 20% w/v. The sugar is especially preferably saccharose and as the sugar alcohol is especially preferably glycerol. However, there can also be used other sugars, such as mannose or the like, or other sugar alcohols, such as hexite, pentite or the like.

In the case of the purification of the enzyme, working is carried out in the usual way in the presence of a complex former, for example ethylenediaminetetraacetic acid (EDTA), and of a mercaptan, such as glutathione or mercaptoethanol. The addition of FAD has also proved to be advantageous.

For high purification according to conventional biochemical fractionation methods, such as ammonium sulphate fractionation, exchanger chromatography and/or molecular sieve fractionation, these can be used in any desired manner. However, it is important always to work in the presence of the above-mentioned digestion buffer. Preferably to the supernatant of the polyethyleneimine precipitation there is added so much weakly alkaline anion exchanger that some nitrate reductase activity still remains in the solution, thus not all of the enzyme activity is bound to the exchanger, and the exchanger is then eluted by increasing the ion concentration. Appropriate weakly alkaline anion exchangers include, for example, those with diethylaminoethanol groups bound to appropriate carrier materials, such as agarose, cellulose and the like.

For chromatographic enrichment, an aromatic-substituted, cross-linked agarose has proved to be especially preferable and such an enrichment step is, therefore, preferred in the scope of the present invention, a purification over phenyl-sepharose being especially preferred.

Furthermore, for the removal of impurities, it is preferred, before or after the anion exchanger treatment and/or of the chromatography, to precipitate out the enzyme by the addition of ammonium sulphate and then again to dissolve the precipitate in digestion buffer for the further working up.

Other enrichment steps which can be used for obtaining the enzyme according to the present invention include affinity chromatography on cytochrome C-containing agarose, for example cytochrome C from horse heart coupled to Sepharose CL6B, to coloured ligands, for example blue Sepharose or FAD-sepharose. However, purification on phenyl-sepharose is especially preferred.

The enzyme from mould fungus especially preferably used for the process according to the present invention has, in a native state, a molecular weight of about 200,000, contains FAD and molybdenum and has a $K_M$ towards nitrate of about $3.2 \times 10^{-4}$M. The determination of the molecular weight takes place by gel filtration.

As zwitterionic buffer, in the scope of the present invention there is preferred a Good buffer. As Good buffer, there is, in turn, especially preferred Hepes buffer. For carrying out the lyophilisation, the enzyme is either precipitated out, for example by the addition of ammonium sulphate, and then taken up in the zwitterionic buffer, or the solution of the enzyme in the digestion buffer is dialysed against the zwitterionic buffer. The zwitterionic buffer is preferably used in a 0.01 to 0.2 molar concentration and especially preferably in a 0.02 to 0.1 molar concentration. It preferably contains small amounts of complex former, for example 0.1 to 50 mM EDTA, small amounts of FAD, especially of from 1 to 30 $\mu$M, and a sulphhydryl compound, preferably in a concentration of from 0.5 to 10 mM, and adjusted with an appropriate base, for example an aqueous solution of sodium hydroxide, to a pH value of from 6.5 to 9 and preferably of from 7 to 8.

The enzyme according to the present invention has a pH optimum of 7.5 and at 35° C. in a 50 mM potassium phosphate buffer of pH 7.5 is stable in the case of incubation for 10 minutes.

The substrate specificity is 100% for nitrate, 0.12% for nitrite, 100% for NADPH and 13% for NADH.

Inhibitors are nitrite at more than $10^{-4}$M (product inhibition), $Mn^{2+}$, $Fe^{2+}$, $Cu^{2+}$, $Fe^{3+}$ (in the absence of EDTA), $CN^-$ and azide.

For use for the determination of nitrate, the nitrate reductase according to the present invention, which is present in a lyophilised state and contains a zwitterionic buffer as described hereinbefore in detail, is dissolved in a nitrogenous heterocyclic buffer with a pH value of from 6.5 to 9 and, therefore, in a reconstituted state, contains not only the zwitterionic buffer but also the nitrogenous heterocyclic buffer.

Consequently, the reagent according to the present invention for the determination of nitrate in dissolved form is characterised by a content of nitrate reductase, as hereinbefore defined, NAD(P)H, zwitterionic buffer of pH 7 to 9 and nitrogenous-heterocyclic buffer of pH 6.5 to 9. For carrying out the nitrate determination, only the reconstituted reagent is added to the nitrate-containing sample and the oxidation of NAD(P)H is determined by measurement of the decrease of the reduced co-enzyme or of the increase of the oxidised co-enzyme. The nitrogenous heterocyclic buffer is preferably imidazole buffer, pyrazole buffer or pyridine buffer, imidazole buffer being especially preferred. The preferred pH value is from 7.0 to 7.8 and the preferred buffer concentration in the reconstituted soluble reagent is from 20 to 50 mmole/liter.

As further component, the reagent according to the present invention preferably contains superoxide dismutase (SOD), preferably in an amount of from 10 to 1000 Unites/ml. of dissolved reagent. Furthermore, it preferably contains several or all of the additives mentioned above for the digestion buffer in the amounts there given.

The following Examples are given for the purpose of illustrating the present invention:

EXAMPLE 1

A) Digestion 9 kg. of filtered off biomass of Asperqillus spec. DSM 1729 are taken up in 50 liters of ice-cold buffer consisting of 0.05M tris/tartaric acid buffer containing 5 mM EDTA, 5 µM FAD and 2 mM mercaptoethanol (pH 7.5). The suspension is homogenised and digested by means of high pressure dispersion (600 bar). 10% Glycerol, 10 µg. PMSF/liter of liquid and 15 µg. benzamidine/liter of liquid are added to the digested biomass and the pH is adjusted to 7.5 with 1M tris base.
Volume: 70 liters
SU activity: 75 KU
SA about 0.12 U/mg.

B) Polymine-P separation

The liquid from step A is mixed, with stirring, after preliminary samples (with in each case 4%, 6%, 8%, 10% of a 1% polymine-P solution) with so much polymine-P that 85% of activity remains in the supernatant. After 15 minutes, it is filtered, the precipitate is discarded and the filtrate is mixed with 7 mg. PMSF and 15 mg. benzamidine per liter of liquid.
Volume: 70 liters
SU activity: 70 KU

C) DEAE-Sephadex batch

Into the filtrate from step B, after preliminary samples (2%, 3%, 4%), so much DEAE-Sephadex is stirred in that more than 10% of activity remains in the supernatant. The exchanger is filtered off and washed with 3 liters of tris/tartaric acid buffer containing 5 mM EDTA, 5 µM FAD and 2 mM mercaptoethanol (pH 7.5). Elution takes place by the addition of 0.5M sodium chloride to the wash buffer (with in all 3×3 liters). The eluates are combined, mixed with 7 mg. PMSF and 15 mg. benzamidine per liter and put in a cool place.
Volume: about 9 liters
SU activity 65 KU.

D) Ammonium sulphate precipitation

The eluate from step C, after preliminary samples (2.0M, 2.2M, 2.4M), is mixed with solid ammonium sulphate until less than 5% of the activity remains in the supernatant. The precipitate is filtered off and the clear supernatant is discarded.

E) Phenyl-Sepharose chromatography

The ammonium sulphate precipitate from step D is taken up in 1 liter tris/tartaric acid buffer (0.05M), containing 5 mM EDTA, 5 µM FAD, 2 mM mercaptoethanol, 10% v/v glycerol and 1M ammonium sulphate (pH 7.5) and mixed with 7 mg. PMSF and 15 mg. benzamidine per liter and possible turbidity centrifuged off.
Volume: 1.4 liters
SU activity: 45 KU
SA: 1.7 U/mg.

The enzyme solution is applied to a 2 liter phenyl-Sepharose column (column 10×29 cm., equilibrated with 0.05M tris/tartaric acid buffer (pH 7.5) containing 5 mM EDTA, 5 µM FAD, 2 mM mercaptoethanol, 10% v/v glycerol and 1M ammonium sulphate). Washing takes place with 3 liters of the above-mentioned buffer.

Elution is carried out with a gradient consisting of

A: 2 liters of buffer like the wash buffer but containing 0.5M ammonium sulphate
B: 2 liters of buffer like the wash buffer but containing 5 mM ammonium sulphate.

Fractions with an activity greater than 5 U/ml. are combined and mixed with 7 mg. PMSF and 15 mg. benzamidine per liter.
Volume: 2.5 liters
SU activity: 36 KU
SA: 4 U/mg.

F) Ammonium sulphate concentration and dialysis

The eluate from Step E is precipitated out with up to 2.4M solid ammonium sulphate, centrifuged and the clear supernatant discarded. The precipitate is taken up in 250 ml. 0.05M tris/tartaric acid buffer containing 5 mM EDTA, 5 µM FAD, 2 mM mercaptoethanol and 10% glycerol (pH 7.5) and mixed with 7 mg. PMSF and 15 mg. benzamidine per liter.

G) Dialysis

The solution from step F is dialysed against 3×5 liters 0.05M HEPES buffer, containing 5 mM EDTA, 5 µM FAD and 2 mM mercaptoethanol (pH 7.5; adjusted with 1N aqueous sodium hydroxide solution).

The dialysate is diluted with dialysis buffer to 60 U/ml., made up with 95 µM FAD and 2 mM GSH and mixed with 80 mg. Ficoll per ml. of enzyme solution. The pH value is adjusted with 1M tris base to 7.5, filtered until substantially free of micro-organisms, frozen and lyophilised.
Yield: about 50 g. lyophilisate
SU activity: 25 KU (30% from initial 1 g. of protein)
activity: 0.5 U/mg. lyophilisate
specific activity: 10 U/mg. protein
foreign activities: NADPH oxidase 0.7%; NADPH-dependent ADH: 0.8%; nitrite reductase: 0.2%
Storage at −20° C.

EXAMPLE 2

Nitrate determination

Test conditions:
Wavelength: (Hg) 365 nm, (Hg) 334 nm, 339 nm; layer thickness: 1 cm.; test volume 2.75 ml.; temperature: 20°–25° C.; measurement against air.
Measurement:

| Into cuvettes pipette in the test | sample | blank | concentrations |
|---|---|---|---|
| K phosphate (0.1 mole/l.; pH 7) | 1.00 ml. | 1.00 ml. | phosphate 35 mmole/l. |
| FAD ($10^{-4}$ mole/l.) | 0.10 ml. | 0.10 ml. | FAD 3.6 µmole/l. |
| NADPH (c = 10 mg./ml.) | 0.05 ml. | 0.05 ml. | NADPH 175 µmole/l. |
| sample (e.g. $KNO_3$) | 0.05 ml. | — | $NO_3^-$ up to 140 µmole/l. |
| water | 1.50 ml. | 1.55 ml. | | mix, leave to stand for about 3 minutes at ambient temperature and measure $E_1$

| nitrate reductase (~6 U/ml.) | 0.05 ml. | 0.05 ml. | NR about 115 U/l. |
|---|---|---|---| mix; leave to stand about 20 to 30 minutes at ambient temperature and measure $E_2$.

Calculate extinction differences $(E_1-E_2)$ of sample and blank:

$$\Delta E_{(nitrate)} = (E_1 - E_2)_{sample} - (E_1 - E_2)_{blank}$$

Calculation $$C\ [g./l.] = \frac{V \times MW \times \Delta E}{\epsilon \times d \times v \times 1000}$$

for nitrate:

- c = concentration of nitrate in the sample solution (g./liter)
- V = test volume in ml. (here 2.75 ml.)
- MW = molecular weight (here nitrate = 62.00 g./mole)
- $\Delta E$ = extinction (see above)
- $\epsilon$ = extinction coefficient at
  - 334 nm (Hg) = 6.18   $1 \times$ mmole$^{-1} \times$ cm$^{-1}$
  - 339 nm = 6.3   $1 \times$ mmole$^{01} \times$ cm$^{-1}$
  - 365 nm (Hg) = 3.5   $1 \times$ mmole$^{-1} \times$ cm$^{-1}$
- d = layer thickness of the cuvette (here 1 cm.)
- v = sample volume (here 0.05 ml.)

c = $\frac{2.75 \times 62.0 \times \Delta E}{\epsilon \times 1 \times 0.05 \times 1000} = \frac{3.410}{\epsilon} \times \Delta E$ [g. nitrate in sample solution]

EXAMPLE 3

Nitrate determination

Test conditions:

Wavelength: (Hg) 365 nm, (Hg) 334 nm, 339 nm; layer thickness 1 cm.; test volume 2.77 ml.; temperature: 20°–25° C.; measurement against air.

Measurement:

| into cuvette pipette | sample | blank | concentration in the test |
|---|---|---|---|
| imidazole (0.1 mole/l.; pH 7.3) | 1.00 ml. | 1.00 ml. | imidazole 35 mmole/l. |
| FAD ($10^{-4}$ mole/l.) | 0.10 ml. | 0.10 ml. | FAD 3.6 $\mu$mole/l. |
| NADPH (c = 10 mg./ml.) | 0.05 ml. | 0.05 ml. | NADPH 175 $\mu$mole/l. |
| superoxide dismutase (6 mg./ml.) | 0.02 ml. | 0.02 ml. | SOD 217 U/l. |
| sample (e.g. KNO$_3$) | 0.05 ml. | — | NO$_3^-$ up to 140 $\mu$mole/l. |
| water | 1.50 ml. | 1.55 ml | | mix, leave to stand for about 3 minutes at ambient temperature and measure $E_1$

| nitrate reductase (~6 U/ml.) | 0.05 ml. | 0.05 ml. | NR about 115 U/l. |
|---|---|---|---| mix, leave to stand for about 30 to 40 minutes at ambient temperature and measure $E_2$.

Calculate extinction differences $(E_1-E_2)$ of sample and blank.

$$\Delta E_{(nitrate)} = (E_1 - E_2)_{sample} - (E_1 - E_2)_{blank}$$

Calculation c [g. NO$_3$/l. sample solution] = $\frac{V \times MW \times \Delta E}{\epsilon \times d \times v \times 1000}$ for nitrate:
- c = concentration of nitrate in the sample solution (g./liter)
- V = test volume in ml. (here 2.77 ml.)
- MW = molecular weight (here nitrate = 62.00 g./mole)
- E = extinction difference (see above)
- $\epsilon$ = extinction coefficients of NADPH at:
  - 334 nm (Hg) = 6.18   $1 \times$ mmole$^{-1} \times$ cm$^{-1}$
  - 339 nm = 6.3   $1 \times$ mmole$^{-1} \times$ cm$^{-1}$
  - 365 nm (Hg) = 3.5   $1 \times$ mmole$^{-1} \times$ cm$^{-1}$
- d = layer thickness of the cuvette (here 1 cm.)
- v = sample volume (here 0.05 ml.)

c = $\frac{2.77 \times 62.00 \times \Delta E}{\epsilon \times 1 \times 0.05 \times 1000} = \frac{3.435}{\epsilon} \times \Delta E$ [g. nitrate/liter sample solution]

We claim:

1. A stabilized NAD(P)H-dependent, soluble nitrate reductase enzyme of the assimilartory type, having a molecular weight of about 90,000 daltons as determined by SDS electrophoresis wherein said nitrate reductase enzyme retains greater than 60% residual activity after 3 weeks at 35° C. and is obtainable by a method which comprises:
   (a) preparing a suspension of a comminuted biological starting material having nitrate reductase activity in a tris/tartaric acid buffer at a pH of from 7 to 8.5;
   (b) adding a soluble polyethyleneimine thereto in an amount sufficient to form a precipitate containing from 10 to 20% of nitrate reductase activity of said suspension and a supernatant containing from 80 to 90% of nitrate reductase activity of said suspension;
   (c) separating precipitate from supernatant;
   (d) fractionating said supernatant in a tris/tartaric acid buffer to form a solution containing said nitrate reductase enzyme;
   (e) dialyzing said solution to separate said nitrate reductase enzyme therefrom; and
   (f) lyophilizing said nitrate reductase enzyme in a zwitterionic buffer.

2. Reagent for the determination of nitrate, which comprises the nitrate reductase enzyme of claim 1, NAD(P)H, a zwitterionic buffer (pH 7 to 9 ) and a nitrogenous heterocyclic buffer (pH 6.5 to 9).

3. Reagent of claim 2 wherein the zwitterionic buffer is a good buffer.

4. Reagent of claim 2 or 3, wherein the nitrogenous heterocyclic buffer is selected from the group consisting of an imidazole buffer, a pyrazole buffer and a pyridine buffer.

5. Reagent of claim 2 or 3, wherein said reagent has a pH value of from 7.0 to 7.8 and the buffer concentration of said reagent ranges from 20 to 50 mmole.

6. Reagent of claim 2 or 3, which further contains superoxide dismutase.

7. Reagent of claim 2 or 3 which further comprises at least one additive selected from the group consisting of a protease inhibitor, flavin adenine dinucleotide, a sugar and a sugar alcohol.

8. A process for preparing the stabilized, NAD(P)H-dependent soluble nitrate reductase enzyme of claim 1, comprising:
   (a) preparing a suspension of a comminuted biological starting material having nitrate reductase activity in a tris/tartaric acid buffer at a pH of from 7 to 8.5;
   (b) adding a soluble polyethyleneimine thereto in an amount sufficient to form a precipitate containing from 10 to 20% of nitrate reductase activity of said suspension and a supernatant containing from 80 to 90% of nitrate reductase activity of said suspension;

(c) separating precipitate from supernatant;

(d) fractionating said supernatant in a tris/tartaric acid buffer to form a solution containing said nitrate reductase enzyme;

(e) dialyzing said solution to separate said nitrate reductase enzyme therefrom; and (f) lyophilizing said nitrate reductase enzyme in a zwitterionic buffer.

9. The process of claim 8, wherein a protease inhibitor is added to the buffer.

10. The process of claim 8, wherein flavin adenine dinucleotide is added to the buffer.

11. The process of claim 8, wherein a sugar or sugar alcohol is added to the buffer.

12. The process of claim 8 which further comprises adding weakly alkaline anion exchanger to the supernatant of the polyethyleneimine precipitation such that nitrate reductase activity still remains in the solution, and eluting the exchanger using increasing ion concentration.

13. The process of claim 8 further comprising chromatographing said solution over aromatic-substituted, cross-linked agarose.

* * * * *

UNITED STATES PATENT AND TRADEMARK OFFICE
CERTIFICATE OF CORRECTION

PATENT NO. : 5,169,758
DATED : December 8, 1992
INVENTOR(S) : Stephan Fischer, et al It is certified that error appears in the above-indentified patent and that said Letters Patent is hereby corrected as shown below:

Column 3, line 14; change "Ascerqillus" to --Aspergillus--.
        line 4; change "Aspercillus" to --Aspergillus--.
Column 8, claim 3, line 2, change "good" to --GOOD--.

Signed and Sealed this

Twenty-ninth Day of March, 1994

Attest:

BRUCE LEHMAN

Attesting Officer     Commissioner of Patents and Trademarks